US00PP36260P2

(12) United States Plant Patent
Koning

(10) Patent No.: US PP36,260 P2
(45) Date of Patent: Nov. 19, 2024

(54) ***ZAMIOCULCAS* PLANT NAMED 'Queen'**

(50) Latin Name: *Zamioculcas zamiifolia*
Varietal Denomination: Queen

(71) Applicant: L. Koning Beheer B.V., Nuis (NL)

(72) Inventor: Lammert Koning, Nuis (NL)

(73) Assignee: L. Koning Beheer B.V. (NL)

( * ) Notice: Subject to any disclaimer, the term of this patent is extended or adjusted under 35 U.S.C. 154(b) by 0 days.

(21) Appl. No.: 18/540,475

(22) Filed: Dec. 14, 2023

(51) Int. Cl.
*A01H 5/12* (2018.01)
*A01H 6/10* (2018.01)

(52) U.S. Cl.
USPC ..... Plt./373

(58) Field of Classification Search
USPC ..... Plt./373
See application file for complete search history.

*Primary Examiner* — Susan McCormick Ewoldt
(74) *Attorney, Agent, or Firm* — Cassandra Bright

(57) ABSTRACT

A new and distinct cultivar of *Zamioculcas* plant named 'QUEEN' is disclosed, characterized by fast growing plants, and larger leaves than typical of the species. The new variety is a *Zamioculcas*, typically produced as an indoor ornamental plant.

2 Drawing Sheets

Figure 1:
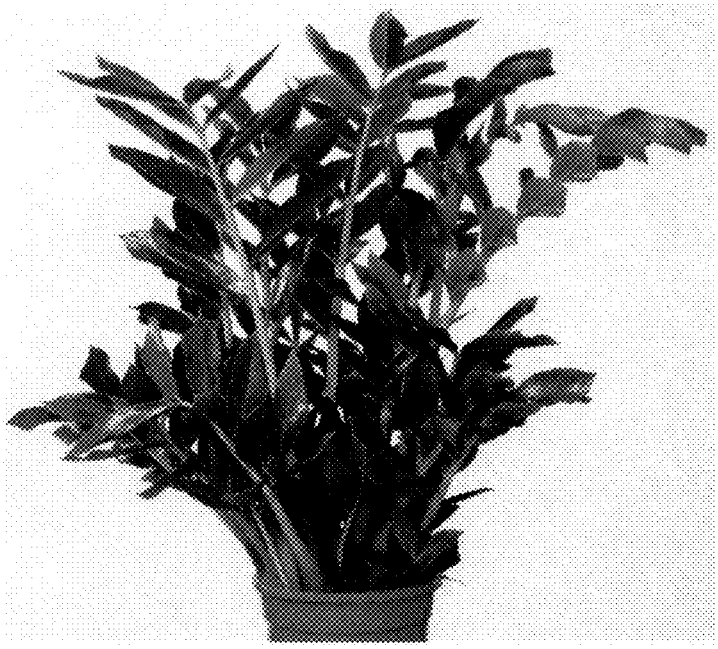

Latin name of the genus and species: *Zamioculcas zamiifolia*.

Variety denomination: 'Queen'.

BACKGROUND OF THE INVENTION

The new *Zamioculcas* 'Queen' is a naturally-occurring branch mutation from an unnamed, unpatented selection of *Zamioculcas zamiifolia*. The new *Zamioculcas* was discovered and selected by the inventor at a nursery in Erica, the Netherlands in the year 2021.

Asexual reproduction of the new cultivar by vegetative cuttings was first performed in May of 2022 in Erica, the Netherlands, and has shown *Zamioculcas* 'Queen' to be stable and true to type in successive generations.

SUMMARY OF THE INVENTION

The cultivar 'QUEEN' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'QUEEN'. These characteristics in combination distinguish 'QUEEN' as a new and distinct *Zamioculcas* cultivar:

1. Plants grow much quicker than the species itself. Plants of 'Queen' are saleable in a 17 cm pot in 20 to 25% less time than plants of the species.
2. Large leaflets, on average 12 cm in length; the species has an average leaflet length of 7.5 cm.
3. Plants make more shoots per leaf-cutting than the species. A 17 cm commercially produced pot of 'Queen' requires 4 cuttings per pot; a 17 cm commercially produced pot of the species requires 5 cuttings per pot.

PARENT COMPARISON

Plants of the new cultivar 'QUEEN' are similar to the parent, an unpatented, unnamed, *Zamioculcas zamiifolia* in most horticultural characteristics. However, the new variety, 'QUEEN' differs from the parent in the following characteristics:

1. Leaves of the new variety are almost twice the size of leaves of the parent variety.
2. Leaves of the new variety are long, elongated, with a pointed end. Leaves of the parent are shorter, less elongated, with a more rounded end.
3. Leaf-stem color of the new variety is light green-grey, while the leaf-stem color of the parent is green.
4. Plants of the new variety produce many more shoots than plants of the parent variety.
5. Plants of the new variety grow 20 to 25% faster than plants of the parent variety.

COMMERCIAL COMPARISON

*Zamioculcas zamiifolia* 'QUEEN' can be compared with the commercial variety *Zamioculcas zamiifolia* 'HANSOTI13', U.S. Plant Pat. No. 26,760. The two varieties are similar in most horticultural characteristics; however, the new variety differs in the following:

1. Leaves of the new variety are larger than leaves of this comparator.
2. Leaves of the new variety are long, elongated, with a pointed end. Leaves of this comparator are shorter, less elongated, with a more rounded end.
3. Plants of the new variety produce many more shoots than plants of this comparator.
4. Leaf-stem color of the new variety is light green-grey, while the leaf-stem color of this comparator is green.

*Zamioculcas zamiifolia* 'QUEEN' can be compared with the commercial variety *Zamioculcas zamiifolia* 'Dowon' U.S. Plant Pat. No. 30,035. The two varieties are similar in most horticultural characteristics; however, the new variety differs in the following:

1. Leaf color of the new variety is green to dark green, while leaf color of this comparator is dark purple.
2. Leaves of the new variety are larger than leaves of this comparator.

3. Leaves of the new variety are long, elongated, with a pointed end. Leaves of this comparator are shorter, less elongated, with a more rounded end.
4. Plants of the new variety produce many more shoots than plants of this comparator.
5. Leaf-stem color of the new variety is light green-grey, while the leaf-stem color of this comparator is green.

BRIEF DESCRIPTION OF THE PHOTOGRAPHS

The accompanying colored photographs illustrate the overall appearance of the new *Zamioculcas* showing the colors as true as it is reasonably possible to obtain in colored reproductions of this type. Colors in the photographs may differ slightly from the color values cited in the detailed botanical description which accurately describe the colors of the new *Zamioculcas*.

FIG. 1. comprises a side perspective view of a typical plant of 'QUEEN'.

Figure 2:
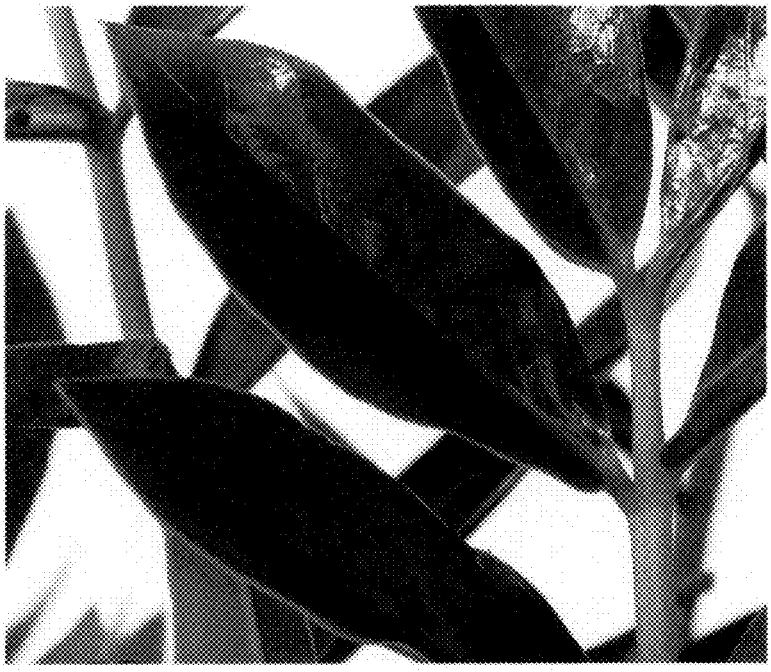

FIG. 2 is a close-up view of typical foliage of 'QUEEN'.

DETAILED BOTANICAL DESCRIPTION

The aforementioned photographs and following observations, measurements and values describe plants of the new *Zamioculcas* grown in Erica, the Netherlands, in a greenhouse. During the production of the plants, day temperatures ranged from 20° to 26° C., night temperatures ranged from 20° to 26° C., and light levels under diffuse plastic and 50% shade net.

Plants had been growing in 17 cm containers for about 40 weeks when the photographs and the description were taken. In the detailed description, color references are made to The Royal Horticultural Society Colour Chart, 2015 Edition, except where general terms of ordinary dictionary significance are used.

Botanical classification: *Zamioculcas zamiifolia* 'QUEEN'.

PROPAGATION

Typical Method: Cuttings are placed directly in the end-pot.

Time to Finishing: About 40 weeks from propagation to saleable plant.

Root Description:

*Structures*.—Tubers.
*Shape*.—Irregular broad oblong-ovoid.
*Length*.—Average 7.2 cm.
*Diameter*.—Average 5.2 cm.
*Texture*.—Smooth, glabrous, matte, very fleshy.
*Color*.—Near RHS Greyed-Green 197D.

PLANT

Plant type: Perennial potted plant.

Plant habit: Compound leaves grow directly from the base, no branches present.

Plant shape: Obovate to oblong.

Plant height: About 51.5 cm.

Plant spread: About 56.5 cm.

Growth rate: Moderate.

Vigor: Moderately high.

Branching: Growing in clumps, compound leaves grow directly from base, no main branches and lateral branches present.

Number of clumps: Average 5 per plant; average 5 per year.

FOLIAGE

Leaf:

*Arrangement*.—Alternate, compound, growing directly from the base.
*Quantity*.—Average 5 leaves per clump.
*Whole Leaf Shape*.—Broad oblong, slightly carinate.
*Whole Leaf Aspect*.—Average angle of 15° to vertical.
*Whole Leaf Length*.—Average 51.5 cm.
*Whole Leaf Width*.—Average 21.2 cm.

Leaflet:

*Shape*.—Narrow elliptic to oblanceolate.
*Quantity*.—Average 12 per leaf.
*Aspect*.—Average angle of near 80° to rachis.
*Base*.—Rounded to short attenuate.
*Apex*.—Acute with a mucronulate tip.
*Margin*.—Entire, very slightly to moderately coarsely undulate.
*Length*.—Average 12.1 cm.
*Width*.—Average 3.9 cm.
*Texture*.—Both sides smooth, glabrous, leathery.
*Rugosity*.—Both sides non-rugose.
*Luster*.—Both sides highly glossy.
*Pubescence*.—None.
*Color*.—Young foliage upper side: Blend of RHS Yellow-Green 143B and 144A. Young foliage under side: RHS Yellow-Green 144A, veins 145A. Mature foliage upper side: Blend of RHS Green NN137A and Yellow-Green 147A. Mature foliage under side: RHS Yellow-Green 143A and 146A.
*Venation*.—Type: Pinnate. Color: Upper side: RHS Yellow-Green 143C. Under side: RHS Yellow-Green 146D.

Petiole:

*Arrangement*.—Leaves consisting of a rachis, leaflets connected to rachis with petiolules.
*Average Length*.—Rachis: 35 cm (including geniculum). Petiolules: 0.4 cm.
*Average Diameter*.—Rachis: 1 cm. Petiolules: Slightly ovoid, average diameter at widest: 1 cm, average diameter at narrowest: 0.9 cm.
*Color*.—Upper Side: Rachis: RHS Yellow-Green 147D, covered with a very thin waxy layer, colored near Greyed-Green 193A. Petiolules: RHS Green 137C.
*Under Side*.—Rachis: RHS Yellow-Green 147D, covered with a very thin waxy layer, colored near Greyed-Green 193A. Petiolules: RHS Green 138A.
*Strength*.—Rachis and petiolules strong.
*Texture*.—Rachis and petiolules smooth and glabrous.
*Luster*.—Rachis matte; petiolules very slightly glossy.

Geniculum:

*Length*.—Approximately 11.8 cm.
*Diameter*.—Thickened at the base and slightly elliptic in cross-section, average diameter at widest: 3.1 cm, average diameter at narrowest: 2.7 cm.
*Color*.—RHS Yellow-Green 146A and 147B.

Stipule:

*Arrangement*.—A leafy stipule of papery texture is present at the base of each main stem.
*Shape*.—Narrow ovate to lanceolate.
*Length*.—Average 9.5 cm.
*Width*.—Average 4.2 cm.

*Top*.—Mucronulate.
*Base*.—Broad cuneate.
*Color*.—RHS Greyed-Orange 164B; 164A towards the top; veined Brown 200B.

OTHER CHARACTERISTICS

Flower: Not observed to date.
Disease Resistance: Similar resistance and susceptibility to the normal diseases found in *Zamioculcas* have been observed.
Drought and Cold Tolerance: USDA hardiness zones 10 to 13. Tolerant from 5° to 40° C. Moderate tolerance to rain and wind.
Fruit/Seed Production: No fruits/seeds detected to date.

What is claimed is:

1. A new and distinct cultivar of *Zamioculcas* plant named 'QUEEN' as herein illustrated and described.

* * * * *